US00RE47388E

(19) United States
(12) Reissued Patent
Fukushima et al.

(10) Patent Number: US RE47,388 E
(45) Date of Reissued Patent: May 14, 2019

(54) AGENTS FOR ALLEVIATING SIDE EFFECTS

(71) Applicant: TAIHO PHARMACEUTICAL CO., LTD., Tokyo (JP)

(72) Inventors: Masakazu Fukushima, Tokyo (JP); Noriyuki Yamamoto, Tokyo (JP); Norihiko Suzuki, Tokyo (JP)

(73) Assignee: TAIHO PHARMACEUTICAL CO., LTD., Tokyo (JP)

(21) Appl. No.: 15/684,291

(22) Filed: Aug. 23, 2017

Related U.S. Patent Documents

Reissue of:
(64) Patent No.: 6,479,500
Issued: Nov. 12, 2002
Appl. No.: 09/701,041
PCT Filed: Mar. 16, 2000
PCT No.: PCT/JP00/01607
§ 371 (c)(1),
(2) Date: Nov. 22, 2000
PCT Pub. No.: WO00/56337
PCT Pub. Date: Sep. 28, 2000

(30) Foreign Application Priority Data

Mar. 23, 1999 (JP) ..... 11-77579

(51) Int. Cl.
*A61K 31/506* (2006.01)
*A61K 31/505* (2006.01)
(Continued)

(52) U.S. Cl.
CPC ..... *C07D 403/06* (2013.01); *A61K 9/0019* (2013.01); *A61K 9/0031* (2013.01);
(Continued)

(58) Field of Classification Search
CPC .... C07D 403/06; A61K 33/24; A61K 31/513; A61K 31/4745; A61K 45/06;
(Continued)

(56) References Cited

U.S. PATENT DOCUMENTS 5,744,475 A 4/1998 Yano et al. ..... 514/274

FOREIGN PATENT DOCUMENTS

EP 0 884 051 12/1998 ..... A61K 31/505
EP 0884051 12/1998
(Continued)

OTHER PUBLICATIONS

International Search Report dated Jun. 13, 2000 in PCT/JP00/01607 filed Jun. 2, 2000.
International Search Report.

*Primary Examiner* — Alan D Diamond
(74) *Attorney, Agent, or Firm* — Oblon, McClelland, Maier & Neustadt, L.L.P.

(57) ABSTRACT

The present invention provides an agent for alleviating side effects caused by use of an anti-tumor agent, which contains 5-chloro-6-(2-iminopyrrolidin-1-yl)methyl-2,4(1H,3H-pyrimidi nedione (1) represented by formula (1):

(1)

or a pharmaceutically acceptable salt thereof. The 5-chloro-6-(2-iminopyrrolidin-1-yl)methyl-2,4(1H,3H)-pyrimidinedione or a pharmaceutically acceptable salt thereof exhibit an inflammatory-suppressing action in the digestive tract and advantageously alleviate diarrhea and loss of body weight concomitant with administration of a chemical for treating cancer without suppressing the anti-tumor effect.
(Continued)

Thus, the compounds of the present invention are of great value as agents for alleviating side effects caused by use of an anti-tumor agent, which enable not only the chemotherapy to be continuedly carried out, but also the body exhaustion to be effectively prevented.

5 Claims, 1 Drawing Sheet

(51) Int. Cl.

| | |
|---|---|
| ***C07D 403/06*** | (2006.01) |
| ***C07D 403/00*** | (2006.01) |
| ***A61K 33/24*** | (2019.01) |
| ***A61K 31/7072*** | (2006.01) |
| ***A61K 9/48*** | (2006.01) |
| ***A61K 9/20*** | (2006.01) |
| ***A61K 9/16*** | (2006.01) |
| ***A61K 9/02*** | (2006.01) |
| ***A61K 9/00*** | (2006.01) |
| ***A61K 45/06*** | (2006.01) |
| ***A61K 31/4745*** | (2006.01) |
| ***A61K 31/513*** | (2006.01) |

(52) U.S. Cl.
CPC ..... *A61K 9/02* (2013.01); *A61K 9/1652* (2013.01); *A61K 9/2018* (2013.01); *A61K 9/4858* (2013.01); *A61K 31/4745* (2013.01); *A61K 31/513* (2013.01); *A61K 31/7072* (2013.01); *A61K 33/24* (2013.01); *A61K 45/06* (2013.01); *Y10S 514/867* (2013.01)

(58) Field of Classification Search
CPC ..... A61K 31/7072; A61K 9/0031; A61K 9/0019; A61K 9/4858; A61K 9/2018; A61K 9/1652; A61K 9/02; Y10S 514/867
See application file for complete search history.

(56) References Cited

FOREIGN PATENT DOCUMENTS

| | | |
|---|---|---|
| WO | 96-30346 | 10/1996 |
| WO | 98-13045 | 4/1998 |

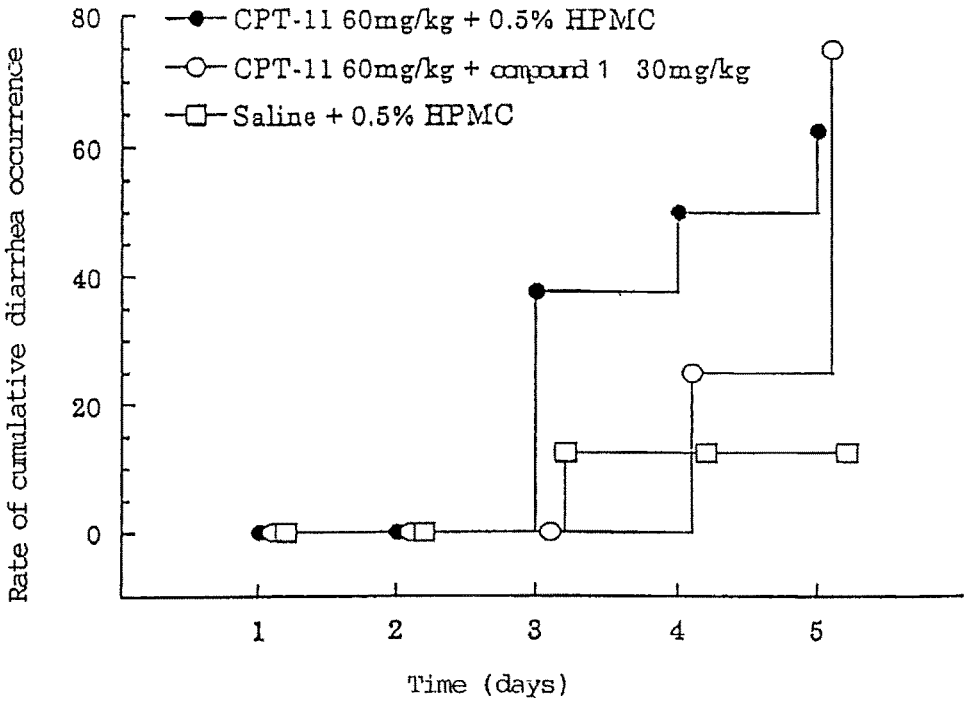
CPT-11 60mg/kg + 0.5% HPMC
CPT-11 60mg/kg + compound 1 30mg/kg
Saline + 0.5% HPMC
Rate of cumulative diarrhea occurrence
80
60
40
20
0
1
2
3
4
5
Time (days)

AGENTS FOR ALLEVIATING SIDE EFFECTS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application is a *Reissue of U.S. Pat. No. 6,479,500, filed Nov. 22, 2000 as U.S. Ser. No. 09/701,041, which is a* 371 of PCT/JP00/01607 filed Mar. 16, 2000 *which is based upon and claims benefit of priority from the prior Japanese Application 11-77579 filed Mar. 23, 1999, the entire contents of which are incorporated herein by reference.*

TECHNICAL FIELD

The present invention relates to an agent for alleviating side effects caused by use of an anti-tumor agent.

BACKGROUND ART

Most drugs employed in chemotherapy to treat cancers act upon proliferating cells to arrest the cell cycle and prevent proliferation of the cells, to thereby terminate proliferation of the cancer tissue or reduce the cancer tissue. However, such drugs also act upon the mucosal cells of the digestive tract, where cell proliferation is active. Therefore, it is well-known that proliferation of mucosal cells in the digestive tract is also prevented, thereby causing shrinkage of mucosal villi; reducing the resistance of the digestive tract against external stimulation such as food; causing inflammatory conditions; and inducing disorders of the digestive tract such as diarrhea and inhibition of nutrient absorption.

When cancer is treated through the administration of an anti-tumor agent, side effects such as nausea, vomiting, diarrhea, and loss of body weight make these drugs very difficult for patients to tolerate. Thus, it is not uncommon in clinical practice that drug administration must be intermitted. In order to alleviate such side effects, compounds have been employed in combination.

For example, a dithiobis (2,2-dimethylpropionamide) derivative is employed with a fluoropyrimidine anti-tumor-agent (Japanese Patent Application Laid-Open (kokal) No. 10-158163); a dithiobis(carboxylic acid) derivative is employed with a fluoropyrimidine anti-tumor agent (Japanese Patent Application Laid-Open (kokai) No.10-158159); conagenin is employed with cancer chemotherapeutic agents such as antimetabolites, alkylating agents, and plant-derived compounds (Japanese Patent Application Laid-Open (kokai) No. 8-165236); a pyrimidine nucleocide phosphorylase inhibitor is employed with 5'-deoxy-5-fluorouridine (Japanese Patent Application Laid-Open (kokai) No. 5-213761); and oxonic acid is employed with a fluoropyrimidine anti-tumor agent (Japanese Patent Application Laid-Open (kokai) No. 5-78249). Of these, only oxonic acid is actually employed in clinic. In a clinical setting, administration of Hange Shashin Tou is discussed so as to prevent delayed diarrhea caused by irinotecan hydrochloride (CPT-11).

However, the capacity of the aforementioned means to alleviate side effects is less than satisfactory.

Thus, an object of the present invention is to provide a drug which can considerably reduce side effects, e.g., such as nausea, vomiting, diarrhea, loss of body weight, and anorexia, caused by administering an anti-tumor agent to an organism, thereby alleviating the side effects suffered by patients and allowing cancer treatment by the use of an anti-tumor agent to continue, which treatment must be intermitted by these side effects.

Disclosure of the Invention

In view of the foregoing, the present inventors have carried out extensive studies from various points of view on 5-chloro-6-(2-iminopyrrolidin-1-yl)methyl-2,4(1H,3H)-pyrimidi nedione or a pharmaceutically acceptable salt thereof, and have found that these compounds can effectively alleviate digestive-tract-related side effects such as nausea, vomiting, diarrhea, loss of body weight, and anorexia, which side effects are caused by an anti-tumor agent. The present invention has been accomplished on the basis of this finding.

Accordingly, the present invention provides an agent for alleviating side effects caused by use of an anti-tumor agent, which comprises, as an active ingredient, 5-chloro-6-(2-iminopyrrolidin-1-yl)methyl-2,4(1H,3H)-pyrimidinedione represented by formula (1):

(1)

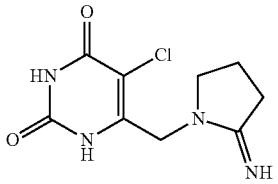

and a pharmaceutically acceptable salt thereof.

The present invention also provides use of the aforementioned compound represented by formula (1) or a pharmaceutically acceptable salt thereof for producing an agent for alleviating side effects caused by use of an anti-tumor agent.

In addition, the present invention also provides a method for alleviating side effects caused by an anti-tumor agent, which comprises administering the aforementioned compound represented by formula (1) or a pharmaceutically acceptable salt thereof.

BRIEF DESCRIPTION OF THE DRAWINGS

FIG. 1 is a chart showing the relationship between cumulative diarrhea occurrence and the number of administration days.

BEST MODE FOR CARRYING OUT THE INVENTION

5-Chloro-6-(2-iminopyrrolidin-1-yl)methyl-2,4(1H,3H)-py rimidinedione is a known compound, and its pharmacological action such as enhancing anti-tumor effects (see International Patent Publication WO/9630346) and cancer metastasis suppressing actions (see International Patent Publication WO/9813045) are known. However, no action to alleviate side effects caused by an anti-tumor agent has been disclosed.

Examples of anti-tumor agents upon which the agent for alleviating side effects of the present invention can act include antimetabolites such as 5-fluorouracil (5-FU), tegafur, carmofur, tegafur-uracil composition (UFT, product of Taiho Pharmaceutical Co., Ltd.), 5-trifluoromethyl-2'-deoxyuridine, 5-fluoro-2'-deoxyuridine, capecitabine, gemcitabine hydrochloride, and methotrexate; plant-derived compounds such as irinotecan hydrochloride (CPT-11), etoposide, vindensine, vincrystine, paclitaxel, and docetaxel; alkylating agents such as cyclophosphamide, itostamide, and ranimustine; anti-cancer antibiotics such as daunorubicin, doxorubicin, pirarubicin, neocarzinostatin, mitomycin C; platinum-containing compounds such as cisplatin (CDDP) and carboplatin; and pharmaceutically acceptable salts thereof. Of these, 5-fluorouracil, tegafur, carmofur, tegafur-uracil composition, 5-trifluoromethyl-2'-deoxyuridine, cisplatin, etoposide, and irinotecan are preferred. Particularly, 5-fluorouracil, 5-trifluoromethyl-2'-deoxyuridine, irinotecan hydrocloride, and cisplastin are most preferred.

No particular limitation is imposed on the pharmaceutically acceptable salts of the compound (1) of the present invention, however, acid-adduct salts reacted with a pharmaceutically acceptable acid are preferred. Examples of acid-adduct salts include salts of an inorganic acid such as hydrochloric acid, sulfuric acid, phosphoric acid, or hydrobromic acid; and salts of an organic acid such as oxalic acid, maleic acid, fumaric acid, malic acid, tartaric acid, citric acid, benzoic acid, acetic acid, p-toluenesulfonic acid, and methanesulfonic acid. Of these, salts of hydrochloric acid orp-toluenesulfonic acid are preferred. Examples of particularly preferred compounds (1) of the present invention or salts thereof include 5-chloro-6-(2-iminopyrrolidin-1-yl)methyl-2,4(1H,3H)-pyrimidi nedione hydrochloride and 5-chloro-6-(2-iminopyrrolidin-1-yl)methyl-2,4(1H,3H)-pyrimidi neone tosylate.

The compound (1) of the present invention or a salt thereof may be formulated singly into a preparation in accordance with the form of administration and may be administered simultaneously or non-simultaneously with an anti-tumor agent which is also formulated into a preparation in accordance with the form of administration. Alternatively, the compound (1) or the salt thereof and the anti-tumor agent may be mixed in advance, formulated into a preparation in accordance with the form of administration, and then administered. When these are administered individually, the compound (1) or the salt there of may be administered arbitrarily before or after administration of the anti-tumor agent.

In the present invention, when the agent for alleviating side effects and the anti-tumor agent are used to treat malignant tumors in mammals including humans, the agent for alleviating side effects and the anti-tumor agent may be formulated into any of the pharmaceutically administrative forms depending on the therapeutic purpose. Examples include oral preparations such as tablets, capsulated tablets, pills, powders, granules, capsules, liquid preparations, suspension preparations, and emulsions; and non-oral preparations such as injections and suppositories. These preparations can be formulated using a pharmaceutically acceptable carrier through a customary method generally known in the art. When the agent is formed into tablets, examples of carriers include vehicles such as lactose, sucrose, sodium chloride, glucose, urea, starch, calcium carbonate, kaolin, crystalline cellulose, and silicic acid; binders such as water, ethanol, propanol, cornstarch, single syrup, glucose liquid, starch liquid, a gelatin solution, carboxymethyl cellulose, shellac, methyl cellulose, hydroxypropyl cellulose, hydroxypropylmethyl cellulose, potassium phosphate, and polyvinyl pyrrolidone; disintegrators such as dry starch, sodium alginate, agar powder, laminaran powder, sodium hydrogen carbonate, calcium carbonate, polyoxyethylene sorbitan fatty acidesters, sodium lauryl sulfate, stearic acid monoglyceride, and lactose; disintegration-inhibitors such as sucrose, stearic acid, cacao butter, and hydrogenated oil; absorption-promoting agents such as quaternary ammonium salts and sodium lauryl sulfate; humectants such as glycerin and starch; absorbents such as starch, lactose, kaolin, bentonite, colloidal silicic acid; lubricants such as purified talc, stearic acid salts, boric acid powder, and polyethylene glycol. Optionally, tablets may be formed into typical coated tablets such as sugar-coated tablets, gelatin-coated tablets, enteric coated tablets, film-coated tablets, double-layered tablets, and multi-layered tablets. When the preparation is formed into pills, examples of carriers include vehicles such as glucose, lactose, starch, cacao butter, hydrogenated vegetable oils, kaolin, and talc; binders such as gum arabic powders, tragacanth powders, gelatin, and ethanol; disintegrators such as laminaran and agar. Capsules are produced using a customary method. For example, the preparation and any of the above carriers are mixed, and the mixture is charged into hard gelatin capsules or soft capsules. When a liquid preparation for oral administration is produced, agents for internal use, syrup agents, and elixirs may be prepared through a customary method using additives such as taste-modifying agents, buffers, stabilizers, and flavoring agents. Examples of taste modifying agents include sucrose, orange peal, citric acid, and tartaric acid. Examples of buffers include sodium citrate. Examples of stabilizers include tragacanth gum, gum arabic, and gelatin. Examples of carriers which can be employed for producing suppositories include polyethylene glycol, cacao butter, higher alcohols, higher alcohol esters, gelatin, and semi-synthesized glycerides. When the preparation is formed into injections, liquid preparations, emulsions, and suspensions are preferably sterilized and made isotonic with blood. When injections are formed, adiluent may be used. Examples of diluents includes water, an aqueous solution of lactic acid, ethyl alcohol, propylene glycol, Macrogol, ethoxylated isostearyl alcohol, polyoxyethylene-modified isostearyl alcohol, and polyoxyethylene sorbitan fatty acid esters. In this case, a sufficient amount of sodium chloride, glucose, or glycerin may be incorporated into the pharmaceutical preparation so as to prepare an isotonic solution, and typical solubilizing agent, buffers, and an esthetics may also be added. In addition, the aforementioned preparations may contain colorants, preservatives, perfumes, flavoring agents, and sweetening agents as well as other pharmaceuticals where desired in accordance with need. No particular limitation is imposed on the amounts of an anti-tumor agent and the compound (1) of the present invention or a salt thereof incorporated into the pharmaceutical preparation of the present invention. The amounts are appropriately predetermined, and each component is incorporated in an amount of approximately 0.01-70 wt. %.

The method for administering the agent for alleviating side effects of the present invention is not particularly limited, and it is appropriately predetermined in accordance with the form of preparation; patient condition, e.g., age and sex; and gravity of the patient's symptoms. For example, tablets, pills, powders, granules, capsules, liquids, suspensions, and emulsions are perorally administered. Injection preparations are intravenously administered singly or in combination with typical auxiliary agents such as glucose and amino acid. Furthermore, injection preparations per se are administered intravenously, arterially, intramuscularly, intradermally, subcutaneously, or intraperitoneally in accordance with need. Suppositories are administered intrarectally.

The dose of the active ingredient of the agent for alleviating side effects of the present invention is appropriately selected in accordance with the directions for use; patient profile, e.g., age and sex; and gravity of the disease. Typically, the compound (1) of the present invention or the pharmaceutically acceptable salt thereof is administered in an amount of approximately 0.01-1000 mg/kg/day, preferably 0.1-100 mg/kg/day. When an anti-tumor agent is incorporated in advance, the target dose of the anti-tumor agent may be approximately 0.01-100 mg/kg/day, preferably 0.05-50 mg/kg/day. The pharmaceutical preparation according to the present invention may be administered in single or divided doses, i.e., 1 to approximately 2-4 doses per day.

Malignant tumors which can be treated by the agent for alleviating side effects of the present invention may be those which can be treated by an anti-tumor agent used in combination with the agent for alleviating side effects of the present invention. Examples of malignant tumors include esophageal cancer, stomach cancer, hepatic cancer, cholecystis-cystic duct cancer, pancreatic cancer, colon cancer, rectal cancer, head and neck cancer, lung cancer, breast cancer, cervical cancer, ovarian cancer, bladder cancer, prostatic cancer, orchioncus, osteo- and soft-part-sarcoma, skin cancer, malignant lymphoma, leukemia, and brain tumors.

EXAMPLES

The present invention will next be described in more detail by way of examples, which should not be construed as limiting the invention thereto.

REFERENTIAL EXAMPLE 1

Preparation of 5-Chloro-6-(2-iminopyrrolidin-1-yl) methyl-2,4-(1H,3H)-pyrimidinedione Hydrochloride (Compound 1)

(1) Sulfuryl chloride (120 ml) was added dropwise to a suspension of 6-chloromethyluracil (163 g) in acetic acid (500 ml) over 20 minutes at room temperature, and the mixture was stirred for an additional 3 hours at room temperature. The resultant solution was poured into iced water (500 ml), and then precipitated crystals were collected through filtration, to there by obtain 182.3 g of 5-chloro-6-chloromethyluracil (92% yield).

Melting Point: ≥225° C. (Decomposed), NMR spectral data (DMSO-$d_6$) δ 4.46 (2H, s), 11.57 (1H, s), 11.71 (1H, s).

(2) 5-Chloro-6-chloromethyluracil (5.0 g), 2-iminopyrrolidine (6.14 g), and sodium ethoxide (5.24 g) were dissolved in N,N-dimethylformamide (50 ml) and the resultant solution was stirred for 14 hours at room temperature. Subsequently, precipitated crystals were collected through filtration, and the crystals were suspended in water (30 ml). The resultant suspension was neutralized with acetic acid and washed. Subsequently, insoluble matter was collected through filtration and was dissolved in 1N HCl (60 ml). Activated carbon was added to the resultant solution and the mixture was subjected to filtration. The filtrate was concentrated under reduced pressure, and the residue was washed with ethanol, followed by filtration, to thereby obtain 2.68 g of the title compound (38% yield).

Melting Point: ≥255° C. (decomposed)

NMR spectral data (DMSO-$d_6$) δ 2.04 (2H, quintet, J=7.6 Hz), 2.87 (2H, t, J=7.6 Hz), 3.59 (2H, t, J=7.6 Hz), 4.69 (2H, s), 9.40 (1H, s), 11.46 (1H, s), 11.73 (1H, s).

REFERENTIAL EXAMPLE 2

Preparation of 5-Chloro-6-(2-iminopyrrolidin-1-yl) methyl-2,4-(1H,3H)-pyrimidinedione Tosylate (Compound 2)

The procedure described in Reference Example 1 was repeated, except that p-toluenesulfonic acid was used instead of 1N HCl, to thereby obtain the title compound (26% yield).

melting point: ≥210° C. (decomposed)

NMR spectral data (DMSO-$d_6$) δ 2.05 (2H, quintet, J=7.7 Hz), 2.29 (3H, s), 2.87 (2H, t, J=7.7 Hz), 3.60 (2H, t, J=7.7 Hz), 4.56 (2H, s), 7.11 (2H, d, J=7.3 Hz), 7.47 (2H, d, J=7.3 Hz), 9.51 (1H, br-s), 11.0-11.8 (2H, very broad).

PREPARATION EXAMPLE 1

| | |
|---|---|
| Compound 1 | 25.0 mg |
| lactose | 8.0 mg |
| crystalline cellulose | 4.0 mg |
| magnesium stearate | 1.0 mg |
| talc | 1.0 mg |
| cornstarch | 3.5 mg |
| hydroxypropylmethyl cellulose | 2.5 mg |
| weight per tablet | 45.0 mg |

Tablets of the above-described formulation were prepared through a routine method.

PREPARATION EXAMPLE 2

| | |
|---|---|
| Compound 2 | 50.0 mg |
| lactose | 85.0 mg |
| cornstarch | 100.0 mg |
| hydroxypropylmethyl cellulose | 3.0 mg |
| weight per sachet | 238.0 mg |

Granules of the above-described formulation were prepared through a routine method.

PREPARATION EXAMPLE 3

| | |
|---|---|
| Compound 2 | 50.0 mg |
| lactose | 24.0 mg |
| crystalline cellulose | 13.0 mg |
| magnesium stearate | 1.0 mg |
| weight per capsule | 88.0 mg |

Capsules of the above-described formulation were prepared through a routine method.

PREPARATION EXAMPLE 4

| Injection | |
|---|---|
| Compound 1 | 50.0 mg |
| water for injection | suitable amount |
| volume per ample | 5 ml |

Injections of the above-described formulation per ample were prepared through a routine method.

PREPARATION EXAMPLE 5

| Suppositories | |
|---|---|
| Compound I | 100.0 mg |
| Witepsol W-35 (Trademark; product of Dynamit Nobel A.G.) | 1400.0 mg |
| weight per suppository | 1500.0 mg |

Suppositories of the above-described formulation per suppository were prepared through a routine method.

PREPARATION EXAMPLE 6

| Anti-tumor Composition for Injection | |
|---|---|
| Compound 2 | 10.0 mg |
| cisplatin | 25.0 mg |
| water for injection | suitable amount |
| weight per ample | 50 ml |

Injections of the above-described formulation per ample were prepared through a routine method.

PREPARATION EXAMPLE 7

| Anti-tumor composition for oral administration | |
|---|---|
| Compound I | 50.0 mg |
| 5-trifluoromethyl-2'-deoxyuridine (FTD) | 12.5 mg |
| lactose | 85.0 mg |
| cornstarch | 100.0 mg |
| hydroxypropylmethyl cellulose | 2.5 mg |
| weight per sachet | 250.0 mg |

Granules of the above-described formulation were prepared through a routine method.

TEST 1

Alleviating Effect on Suppression of Body Weight Increase (a) Preparation of Test Solution—I:

5-Fluorouracil (hereinafter referred to as "5-FU") was suspended in saline so as to obtain a 2.0 mg/ml suspension, and the suspension was stirred by use of a stirrer for about 20 minutes at room temperature. The suspension was treated with sonication for 5 minutes while being cooled with ice, to thereby obtain a test solution containing 5-FU for administration at 20 mg/kg/day.

(b) Preparation of Test Solution—II:

Cisplatin (hereinafter referred to as "CDDP") was suspended in saline so as to obtain a 0.1 mg/ml suspension, and the suspension was stirred by use of a stirrer for about 20 minutes at room temperature. The suspension was treated with sonication for 5 minutes while being cooled with ice, to thereby obtain a test solution containing CDDP for administration at 1.0 mg/kg/day.

(c) Preparation of Test Solution—III:

Compound 1 was suspended in water so as to obtain a 10 mg/ml suspension, and the suspension was stirred by use of a stirrer for about 20 minutes at room temperature. The suspension was treated with sonication for 5 minutes while being cooled with ice, to thereby obtain a test solution containing Compound 1 for administration at 100 mg/kg/day.

(d) Test:

Five-week-old Donryu male rats were divided into a control group and treatment groups so that the average body weights of the groups and the standard deviations (S.D.) of the groups were made to be as close to one another as possible. To each rat of the anti-tumor-agent treatment alone groups, the 5-FU solution or the CDDP solution was intravenously administered once a day for four consecutive days at a daily dose of 1.0 ml per 100 g of body weight. Simultaneously, water was orally administered once a day for four consecutive days at a daily dose of 1.0 ml per 100 g of body weight. To each rat of the combination-administration treatment groups, the 5-FU solution or the CDDP solution was intravenously administered once a day for four consecutive days at a daily dose of 1.0 ml per 100 g of body weight. Simultaneously, to each rat of the combination-administration groups, the solution of Compound 1 was orally administered once a day for four consecutive days at a daily dose of 1.0 ml per 100 g of body weight. To each rat of the control group, saline was intravenously administered once a day for four consecutive days at a daily dose of 1.0 ml per 100 g of body weight. Simultaneously, water was orally administered once a day for four consecutive days at a daily dose of 1.0 ml per 100 g of body weight.

The rats were weighed prior to initiation of administration (day 1) and on the day following the day of final administration (day 5), and the ratio of suppression of body weight increase was calculated by use of the following equation. The results are shown in Table 1.

Test results were statistically analyzed using the Student's "T" test. The marks "*" and "**" mean statistically significant differences from the control groups ((*;$p<0.05$) and (**; $p<0.01$)), and the marks "#" and "##" mean statistically significant differences from the anti-tumor-agent-administration alone groups ((#; $p<0.05$) and (##; $p<0.01$)).

Ratio of suppression of body weight increase (%)= (1−body weight changes of one treatment group/body weight changes of the control group)×100

TABLE 1

| Compounds (dose, mg/kg) | No. of animals | Body weight change (g) | Suppression ratio (%) |
|---|---|---|---|
| Control | 8 | 29.3 ± 3.7 | |
| 5-FU(20) | 8 | 15.6 ± 3.6** | 46.7 |
| 5-FU(20) + Compound 1(100) | 8 | 23.3 ± 4.8*## | 20.7 |
| CDDP(1.0) | 8 | 11.9 ± 5.4** | 59.4 |
| CDDP(1.0) + Compound 1 (100) | 8 | 17.3 ± 5.7**# | 41.1 |

Suppression of body weight increase was confirmed in the rats in the anti-tumor-agent-administration alone groups, in which 5-FU in an amount of 20 mg/kg/day or CDDP in an amount of 1.0 mg/kg/day was administered to each rat for 4 consecutive days. It became apparent that suppression of body weight increase due to the anti-tumor agent was alleviated when Compound 1 was administered in an amount of 100 mg/kg/day in combination with the anti-tumor agent. Moreover, it was confirmed that the occurrence of diarrhea as observed in the combination-administration groups was lower than that of diarrhea as observed in the anti-tumor-agent-administration alone groups.

TEST 2

Delaying Effect on Diarrhea Occurence (a) Preparation of Test Solution—I:

Irinotecan hydrochloride (hereinafter referred to as "CPT-11"; KAMPTO Injection 100 mg/5 ml; product of Yakult Co., Ltd.) was diluted with saline so as to obtain a 6 mg/ml solution for administration at 60 mg/kg/day.

(b) Preparation of Test Solution—II:

Compound 1 was suspended in a 0.5% hydroxypropylmethyl cellulose solution (hereinafter referred to as "0.5% HPMC") so as to obtain a 3 mg/ml suspension, and the suspension was stirred by use of a stirrer for about 20 minutes at room temperature. The suspension was subjected to ultrasound treatment for 5 minutes while being cooled with ice, to thereby obtain a test solution containing Compound 1 for administration at 30 mg/kg/day.

(c) Test:

Five-week-old Donryu male rats were divided into a control group and treatment groups so that the average body weights of the groups and the standard deviations (S.D.) of the groups were made to be as close to one another as possible. To each rat of the anti-tumor-agent treatment alone groups, the CPT-11 solution was intravenously administered once a day for five consecutive days at a daily dose of 1.0 ml per 100 g of body weight. Simultaneously, a 0.5% HPMC solution was orally administered once a day for five consecutive days at a daily dose of 1.0 ml per 100 g of body weight. To each rat of the combination-administration treatment groups, the CPT-11 solution was intravenously administered once a day for five consecutive days at a daily dose of 1.0 ml per 100 g of body weight. Simultaneously, to each rat of the combination-administration groups, the solution of Compound 1 was orally administered once a day for five consecutive days at a daily dose of 1.0 ml per 100 g of body weight. To each rat of the control group, saline was intravenously administered for five consecutive days at a daily dose of 1.0 ml per 100 g of body weight. Simultaneously, a 0.5% HPMC solution was orally administered for five consecutive days at a daily dose of 1.0 ml per 100 g of body weight. Prior to each administration, the stool and anal fecal matter of each rat were observed in order to check the occurrence of diarrhea. The number of rats which had diarrhea at least once during the test period were counted as "diarrhea-rats". The accumulated occurrence of diarrhea was calculated by use of the following equation:

accumulated occurrence of diarrhea (%)=(the number of rats which had diarrhea/the total number of rats)×100

As shown in FIG. 1, diarrhea occurred after the third administration day in rats in the anti-tumor agent administration group, in which CPT-11 in an amount of 60 mg/kg/day was administered every day. It was shown that the event of diarrhea is delayed when Compound 1 was concomitantly administered in an amount of 30 mg/kg/day.

TEST 3

Action on Anti-tumor Action of Cancer Drug (a) Preparation of Test Solution—I:

CDDP was suspended in saline so as to obtain a 0.6 mg/ml suspension, and the suspension was stirred by use of a stirrer for about 20 minutes at room temperature. The suspension was subjected to sonication for 5 minutes while being cooled with ice to thereby obtain a test solution containing CDDP for administration at 6.0 mg/kg/day.

(b) Preparation of Test Solution—II:

Compound 1 was suspended in 0.5% HPMC so as to obtain a 3 mg/ml suspension, 10 mg/ml suspension, and 30 mg/ml suspension, respectively, and each suspension was stirred by use of a stirrer for about 20 minutes at room temperature. Each suspension was subjected to sonication for 5 minutes while being cooled with ice to thereby obtain test solutions containing Compound 1 for administration at 30 mg/kg/day, 100 mg/kg/day, and 300 mg/kg/day, respectively.

(c) Test:

Five-week-old Donryu male rats were divided into a control group and treatment groups so that the average body weights of the groups and the standard deviations (S.D.) of the groups were made to be as close to one another as possible. Yoshida sarcoma ($2\times10^4$ cells/0.1 ml/rat) was subcutaneously transplanted on the back of each rat, and administration was started the day following the day of transplant. To each rat of the CDDP treatment alone groups, the CDDP solution of 6.0 mg/kg was intravenously administered on the first administration day, and a 0.5% HPMC solution was orally administered for seven consecutive days at a daily dose of 1.0 ml per 100 g of body weight. In a similar manner, to each rat of the combination-administration treatment groups, the aforementioned CDDP solution at 6.0 mg/kg was intravenously administered on the first administration day, and a solution of Compound 1 (30 mg/kg/day, 100 mg/kg/day, or 300 mg/kg/day) was orally administered once a day for seven consecutive days at a daily dose of 1.0 ml per 100 g of body weight. To each rat of the control group, saline was intravenously administered on the first administration day in a dose of 1.0 ml per 100 g of body weight. Simultaneously, a 0.5% HPMC solution was orally administered once a day for five consecutive days at a daily dose of 1.0 ml per 100 g of body weight. In order to observe the action of Compound 1 per se, Compound-1-administration alone groups were provided for administration at 30 mg/kg/day, 100 mg/kg/day, and 300 mg/kg/day, respectively.

The rats were weighed on the day of transplantation (day 0) and the day following the day of final administration (day 8), and the suppression ratio of body weight increase was calculated by use of the following equation.

Ratio of suppression of body weight increase (%)=(1−body weight changes of one treatment group/body weight changes of the control group)×100

The weight of the tumor was measured by weighing rats sacrificed on the day following the day of the final administration, and the tumor shrinkage ratio was calculated by use of the following formula.

Ratio of tumor shrinkage (%)=(1−tumor weight changes of one treatment group/tumor weight changes of the control group)×100

The results are shown in Table 2.

TABLE 2

| Compounds (dose, mg/kg) | No. of animals | Tumor weight (g) | Inhibition ratio (%) | Body weight change (g) | Weight change ratio (%) |
|---|---|---|---|---|---|
| Control | 8 | 0.666 ± 0.244 | | 25.9 ± 9.2 | |
| CDDP(6.0) + 0.5% DPW | 8 | 0.162 ± 0.155 | 75.7 | −19.4 ± 8.6 | 174.9 |
| CDDP(6.0) + Compound 1 (30) | 8 | 0.167 ± 0.147 | 74.9 | −2.7 ± 12.8 | 110.4 |
| CDDP(6.0) + Compound 1 (100) | 7 | 0.139 ± 0.130 | 79.1 | −9.1 ± 18.9 | 135.1 |
| CDDP(6.0) + Compound 1 (300) | 8 | 0.158 ± 0.122 | 76.3 | −7.4 ± 16.3 | 128.6 |
| Saline + Compound 1 (30) | 7 | 0.787 ± 0.307 | −18.1 | 29.3 ± 10.2 | −13.1 |
| Saline + Compound 1 (100) | 8 | 0.816 ± 0.329 | −22.4 | 23.9 ± 6.6 | 7.7 |
| Saline + Compound 1 (300) | 7 | 0.829 ± 0.281 | −24.5 | 28.1 ± 6.0 | −8.5 |

Significant inhibition of tumor weight and body weight to the control group has been proven when CDDP alone was administered at a dose of 6 mg/kg. When Compound 1 was administered for seven consecutive days, suppression of body weight was alleviated without affecting the anti-tumor action.

TEST 4

Suppression of Body Weight, and Variation of Inflammatory Cytokine Level in the Small Intestine and the Large Intestine (a) Preparation of Test Solution—I:

5-Trifluoromethyl-2'-deoxyuridine (hereinafter abbreviated as FTD) was suspended in a 0.5% HPMC solution so as to obtain a 20 mg/ml suspension, and the suspension was stirred by use of a stirrer for about 20 minutes at room temperature. The suspension was subjected to sonication for 5 minutes under ice cooling, to thereby obtain a test solution containing HD for administration of 200 mg/kg/day.

(b) Preparation of Test Solution—II:

FTD was suspended in a 0.5% HPMC solution so as to obtain a 20 mg/ml suspension. To the suspension, Compound 1 was added so as to attain a concentration of 9.4 mg/ml. The resultant mixture was stirred by use of a stirrer for about 20 minutes at room temperature, and then subjected to sonication under ice cooling, to thereby obtain a test solution containing FTD and Compound 1 (mol ratio 1:0.5).

(c) Preparation of Test Solution—III:

Compound 1 was suspended in a 0.5% HPMC solution so as to obtain a 10 mg/ml suspension, and the suspension was stirred by use of a stirrer for about 20 minutes at room temperature. The suspension was subjected to sonication for 5 minutes under ice cooling, to thereby obtain a test solution containing Compound 1 for administration of 100 mg/kg/day.

(d) Test:

Eight-week-old male ICR rats were divided into a control group and treatment groups so that the average body weights of the groups and the standard deviations (S.D.) of the groups were made to be as close to one another as possible. To each rat of the FTD treatment alone groups, the FTD solution of 200 mg/kg/day (1.0 ml) was orally administered once a day for eight consecutive days (per 100 g body weight of each rat). To each rat of combination-administration treatment groups, a mixture solution of FTD and Compound 1 was perorally administered once a day for eight consecutive days at a daily dose of 1.0 ml per 100 g of body weight. To each rat of the control group, a 0.5% HPMC solution was perorally administered for eight consecutive days. In order to observe the action of Compound 1 per se, Compound 1-administration alone groups were provided for administration of 100 mg/kg/day.

Measurement of Body Weight Change

The rats were weighed at the previous day of the first administration (day 0) and the following day of the day of final administration (day 9), and the ratio of body weight ratio was calculated by use of the following equation. There sults are shown in Table 3.

Ratio of body weight change (%)=body weight changes/body weight before administration×100

Test results were statistically analyzed in accordance with the Dunnett method ((*; $p<0.05$) and (**; $p<0.01$)).

TABLE 3

| Compounds (dose, mg/kg) | No. of animals | Body weight change (g) | weight change ratio (%) |
|---|---|---|---|
| Control | 6 | 1.4 ± 0.9 | 3.9 |
| FTD(200) | 6 | −1.6 ± 4.7** | −17.6 |
| VID(200) + Compound 1 (94) | 6 | 0.3 ± 0.7 | 0.7 |
| Compound 1 (100) | 6 | 2.4 ± 1.1 | 6.8 |

Administration of solo FTD at a daily dose of 200 mg/kg for eight consecutive days resulted in a decrease ratio of the body weight at the following day of the final administration to that before administration of approximately 18%. The decrease in the body weight was protected by incorporating Compound 1 at a dose of 94 mg/kg/day.

Measurement of Cytokines in the Small Intestine and the Large Intestine

After the aforementioned body weight measurement on the following day of final administration was completed, each rat was anesthetized with ether, and a region of the large intestine 3-6 cm from the anus and the whole jejunoileal portion, i.e., the small intestine from which the duodenum was removed, were collected. Immediately after the collected region were washed with saline, the portions were frozen to preserve at −80° C. Each sample preparation was diluted with a 0.05M phosphate buffer (pH 7.4) so as to attain a tissue concentration of approximately 10% (W/V), and the resultant mixture was homogenized, subjected to sonication, and subjected twice to freeze-thawing. The thus-treated matter was centrifuged at 12,000 g for 15 minutes, and the supernatant was collected to serve as a sample for cytokine measurement.

Cytokines, i.e., IL-1β and mouse IL-6 were measured by use of an ELISA kit for mouse (product of Endogen, Inc.), and the results are shown in Table 4.

Test results were statistically analyzed in accordance with the Dunnett method ((*; $p<0.05$) and (**; $p<0.01$)).

TABLE 4

| (pg/mg protein) | | | |
|---|---|---|---|
| Compounds | Small intestine | Large intestine | |
| (dose, mg/kg) | IL-6 | IL-1β | IL-6 |
| Control | 16.2 ± 5.9 | 23.6 ± 10.0 | 11.1 ± 5.7 |
| FTD(200) | 95.5 ± 19.2** | 77.3 ± 42.1** | 118.0 ± 47.6** |
| FID(200) + Compound 1 (94) | 17.2 ± 11.9 | 14.0 ± 4.0 | 11.3 ± 4.6 |
| Compound 1 (100) | 19.8 ± 9.9 | 23.7 ± 4.6 | 10.7 ± 4.7 |

Administration of FTD at a daily dose of 200 mg/kg/day for eight consecutive days resulted in a high level of inflammatory cytokine IL-6 both in the small intestine and the large intestine as compared with the control group. In addition, the level of IL-1β was elevated in the large intestine. The increase in level of the inflammatory cytokines was inhibited by incorporating Compound 1 at a dose of 94 mg/kg, which is a nearly same level observed in the control group.

INDUSTRIAL APPLICABILITY

5-Chloro-6-(2-iminopyrrolidin-1-yl)methyl-2,4(1H,3H)-pyrimidinedione (1) or a pharmaceutically acceptable salt thereof exhibit a suppressing action against inflammations evoked in the digestive tract after administration of an anti-tumor agent, and advantageously alleviate diarrhea and loss of body weight concomitant with administration of a chemical for treating cancer without suppressing the anti-tumor effect. Thus, the compounds of the present invention are of great value as agents for alleviating side effects caused by use of an anti-tumor agent, which enable not only the chemotherapy to be continuedly carried out, but also the body exhaustion to be effectively prevented.

What is claimed is:

1. A method for alleviating side effects caused by use of an anti-tumor agent *selected from the group consisting of an alkylating agent, a plant-derived compound, an antibiotic, or a platinum containing agent* comprising administering 5-chloro-6-(2-iminopyrrolidin-1-yl)methyl-2,4(1H,3H)-pyrimidinedione represented by formula (1):

(1)

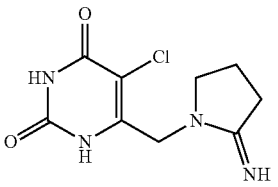

or a pharmaceutically acceptable salt thereof to a patient to whom [an] *the* anti-tumor agent has been administered.

2. A method according to claim 1, wherein the side effect caused by use of the anti-tumor agent is nausea, vomiting, diarrhea, anorexia, or loss of body weight.

[3. A method according to claim 1 or 2, wherein the anti-tumor agent is an antimetabolite, an alkylating agent, a plant-derived compound, an antibiotic, or a platinum-containing agent.]

4. A method according to claim 1 or 2, wherein the anti-tumor agent is [5-trifluoromethyl-2'-deoxyuridine, 5-fluorouracil,] irinotecan hydrochloride[,] or cisplatin.

*5. The method of claim 4, wherein the anti-tumor agent is irinotecan hydrochloride.*

*6. The method of claim 4, wherein the anti-tumor agent is cisplatin.*

* * * * *